United States Patent
Bowden et al.

(10) Patent No.: US 6,552,247 B1
(45) Date of Patent: *Apr. 22, 2003

(54) DISTINCT VARIETY OF BASIL

(75) Inventors: Donald R. Bowden, Oceanside, CA (US); Paul W. Friedman, Del Mar, CA (US)

(73) Assignee: Herb Thyme Farms, Inc., So. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/368,207

(22) Filed: Aug. 4, 1999

Related U.S. Application Data

(60) Provisional application No. 60/095,342, filed on Aug. 4, 1998.

(51) Int. Cl.$^7$ .............................. A01H 1/00; A01H 5/00
(52) U.S. Cl. ...................... 800/265; 800/260; 800/298
(58) Field of Search ................... 800/298, 260, 800/265, 279, 278, 289, 301

(56) References Cited

PUBLICATIONS

Weahsler, D. National Gardening 18(3) : 64–88, Corresponding to pp. 1–6 of Gardener's Supply Co., Jun. 1995.*
Simon et al. Perspectives on New Crops and New Uses, pp. 499–505, J.Janick (Ed), A SHS : Alexandria Press, 1999.*
Park Seed Online Store, "Basil Nufar Hybrid", Jul. 2001.*
Schmitt et al. Plant Disease 15 : 1–4, Dec. 1998.*
Walker, J. Hort Science 30(2) : 292–293, Apr. 1995.*
Rhoades, H. Annals of Applied Nematology 2 : 22–24, Oct. 1998.*
Reuveni et al. Plant Disease 81(9) : 1077–1081, Sep. 1997.*
Davis, J. "In–Row Plant Spacing and Yields of Fresh–Market Basil." 1993, Journal of Herbs, Spices & Medicinal Plants, vol. 2 (1), pp. 35–43.*
Lange, D.L. et al., "Controlled–atmosphere Storage of Sweet Basil." 1998, HortScience, vol. 33(4), pp. 741–743.*
Putlievsky, E. "Temperature and daylength influences on the growth and germination of sweet basil and oregano." 1983, Journal of Horticultural Science, vol. 58(4), pp. 583–587.*
Reuveni, R. et al., "NUFAR: A Sweet Basil Cultivar Resistant to Fusarium Wilt." 1998, HortScience, vol. 33(1), p. 159.*
Santos, B.M. et al., "Effects of Nitrogen and Gibberellic Acid Combinations on Basil Growth." 1998, Soil Crop Sci. Soc. Florida Proc., vol. 57, pp. 99–101.*

* cited by examiner

Primary Examiner—David T. Fox
(74) Attorney, Agent, or Firm—Foley & Lardner; Bernard L. Kleinke

(57) ABSTRACT

The new basil plant is reproduced asexually, with cuttings maturing into transplantable plants in only a few days with a nearly 90% survivability rate. A crop of new basil plants has a die-off rate of typically less that 10% when attacked by Fusarium wilt. High leaf to stem ratio, fast growth, large leaf, and tall plants provide superior production rates.

15 Claims, 3 Drawing Sheets

(3 of 3 Drawing Sheet(s) Filed in Color)

DISTINCT VARIETY OF BASIL

CROSS-REFERENCE TO RELATED APPLICATIONS

This application claims benefit of U.S. provisional patent application No. 60/095,342 filed Aug. 4, 1998, and entitled "A NEW AND DISTINCT VARIETY OF BASIL", which is incorporated herein by reference. This patent application also relates to copending U.S. plant patent application Ser. No. 09/129,027, filed Aug. 4, 1998, and entitled "A NEW AND DISTINCT VARIETY OF BASIL".

BACKGROUND OF THE INVENTION

The field of the present invention is plants. More specifically, the present invention relates to a new and distinct variety of basil plant.

Basil (*Ocimum basilicum*) is a popular herb having cooking and medicinal uses. In cooking, the herb is often used either fresh or dried to impart its distinctive flavor into various dishes, especially Italian cuisine. The most common types of basil for cooking purposes are the Sweet Italian basil varieties. As an herbal medicine, basil is believed to have a soothing effect on the digestive system.

Basil is commonly used in cooking in either a fresh or dried form. Recently, the demand for fresh basil has mushroomed. Not only has there been a general trend in cooking to use fresh ingredients, but modern cooks are discovering the taste advantages of using fresh herbs such as basil. As with the sale of any harvested fresh plant, visual appeal and fresh characteristics are important to obtain maximum commercial value.

Sweet Italian basil is an annual plant that is generally planted for a single harvest season. Each year, therefore, a new crop of Sweet Italian basil is typically seeded. Sweet Italian basil is particularly susceptible to the disease, Fusarium wilt. Fusarium wilt is characterized by damping-off, collapse of the plant, wilting, and a brown dry rot. This disease is caused by any of several fungi of the genus, Fusarium. Fusarium wilt can devastate a stand of basil and there is no known effective remedy. Therefore, if a stand of basil is attacked by Fusarium wilt, the stand is harvested at dramatically reduced levels. Once a stand is infected with Fusarium wilt, a die off of about 70% is typical, thus dramatically reducing the economic value of the crop.

When fully grown, the Sweet Italian basil plant may reach a height of two feet. The plant has green shiny 1–2 inch long leaves and has spikes of white flowers. During its growth period the Sweet Italian basil plant is also susceptible to attack by insects. Particularly problematic is a the root knot nematode. The root knot nematode is an unsegmented worm such as the round worm, and attacks the root system of the Sweet Italian basil. Although not as devastating as Fusarium wilt, the root knot nematode has a significant negative effect on the production levels of that crop.

Sweet Italian basil, being an annual, is generally grown for only a single season and can commonly be harvested eight to ten times. Each time a basil plant is harvested, only selected parts of the foliage are removed for processing and sale. The harvested parts of the basil plant are commonly referred to as "basil tops", even though the harvested parts do not necessarily come only from the top of the plant.

Commercially harvested sweet basil requires careful monitoring of temperatures for optimal production. For example, once temperatures reach approximately 100 degrees, there is a dramatic effect on the turgidity of the cell walls of the plant, causing rapid wilt. Therefore, a commercial basil grower must delay harvesting until more moderate temperatures return, or accept the risk that a substantial amount of the basil harvested in high heat will wilt and have to be discarded.

Once the basil tops have been harvested, they are refrigerated and packaged. The refrigerated packages are shipped to commercial market outlets where they are sold. Once the basil tops have been harvested from the Sweet Italian basil plant, the basil tops can deteriorate rapidly by wilting and turning black. Within a few days after harvesting, the harvested basil tops typically have deteriorated to the point they are no longer fit for sale. Once the basil has deteriorated beyond a point of marketability, it must be discarded by the commercial outlet, thereby being a total economic loss. Sweet Italian basil typically must be sold within only four days after harvest.

The productivity of basil is measured in the pounds of basil tops harvested per acre each month. Since fresh basil is sold by weight, the productivity of a crop of basil is therefore a primary indicator of the economic value for a particular variety. In the peak summer growing season, it is possible to get up to 9,250 pounds per acre per month from a crop of Sweet Italian basil. This productivity drops dramatically to about 3900 pounds per acre per month in the cooler winter months.

Once the growing season has ended, the basil plants are removed and new plantings are grown for the succeeding season. Although typically a crop of Sweet Italian basil is planted from seed, in some rare circumstances, it may be desirable to asexually propagate Sweet Italian basil. However, The Sweet Italian basil plant can be difficult to propagate asexually in quantity as asexually propagated basil plant typically die off at a rate exceeding 60%.

Thereby, known basil plants suffer susceptibility to Fusarium wilt, have a very limited shelf life, and are difficult to propagate.

SUMMARY OF THE INVENTION

Therefore, it is an object of the present invention to provide a basil plant that has superior Fusarium wilt resistance. It is another object of the present invention that the basil plant have a good shelf life and can be easily propagated. It is yet another object of the present invention that the basil plant have increased production characteristics.

To overcome the deficiencies discussed above and meet the objectives, there is provided a novel variety of basil. The new basil plant is reproduced asexually, with cuttings maturing into transplantable plants in only a few days with a nearly 90% survivability rate. A crop of new basil plants has a die-off rate of typically less that 10% when attacked by Fusarium wilt. High leaf to stem ratio, fast growth, large leaf, and tall plants provide superior production rates.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

BEST MODE FOR CARRYING OUT THE INVENTION

Figure 1:
FIG. 1 of the accompanying photographic drawing illustrates the new basil plant growing in an above-ground container. The new plants are shown with a background having 1 foot segmentation for size reference.

Referring now to FIG. 1, there is shown a novel basil plant 10 made in accordance with the present invention. The new basil plant 10 was selected for its unique characteristics and was asexually propagated over several seasons. The resulting variety exhibits substantially superior traits in disease resistance, production, transplant survivability, and shelf life, for example. Further, enhanced small and taste characteristics make the new basil plant exceptionally well suited for human consumption.

As indicated, the present invention relates to a new and distinct variety of basil. This new variety of basil has been successfully asexually reproduced by the above-listed inventors since the spring of 1994. For the planting season 1993, a crop of basil was propagated by seed. At the end of the 1993 growing season, certain plants were selected for their unique characteristics, including not-seen before resistance to Fusarium wilt. These 1993 stock plants were isolated from the remaining crop. Over the next successive planting seasons, cuttings were taken and asexually propagated to increase the number of new basil plants. Throughout this process the plants were identified and segregated from the traditional Sweet Italian basil.

Specifically, the asexual reproduction of the new variety was accomplished by taking softwood cuttings from a strong apical part of the stock new basil plant. The cuttings were at least five inches in length and were chosen such that there was no discoloration in the stem or leaf. Although branch stems are not preferred, they could be used if necessary to increase the number of plants. The cuttings were occasionally misted to maintain their freshness. Immediately prior to planting in the flats, the cuttings were cut back to about a three inch length, thereby reducing the amount of moisture loss caused by the cut. If the leaves of the cutting were excessively large, they were trimmed. A new fresh angled cut was made on the cutting, a rooting hormone applied, and the cutting inserted into soil in a flat.

Once the cutting was in the soil medium, it was necessary to dampen immediately. Care was taken that the soil was tightly placed against the cutting, thereby reducing the air space around the cutting and increasing the contact between the soil and the plant material. Flats having the newly planted cuttings of the new plant were maintained at approximately 80° F., thereby allowing for rapid root development. Frequent and short waterings were given to maintain proper moisture levels. As the roots began to develop, the watering frequency was decreased. Although adequate water is important in the asexual propagation process, care was taken not to over water.

The time necessary for the cuttings to mature into transplantable plants varied depending on the season and temperature. In summer, the new asexually propagated plants went from cutting to plantable plant in only 7 to 10 days, and this period would extend to 14 to 21 days in winter.

A detailed description of the new variety of basil is as follows based upon observation made from the plants grown in Oceanside, California. These plants were grown and asexually reproduced from the spring of 1994 until July of 1998. It has been found to retain its distinctive characteristics through successive asexual propagation.

The new basil plant is particularly easy to asexually reproduce. As indicated above, the new basil plants matured from cuttings to transplantable plants in only 7–10 days in the summer and 14–21 days in the winter. Indeed, the plants could be rooted in less than seven days if temperatures were consistently held between 75 and 90 degrees, and even at 65 degrees the plants could be replanted in only 14 days. Not only was the asexual reproduction faster due to the quick rooting characteristics of the new plant, but the new plant had a survivability rate of approximately 90%. Since known types of basil have a survivability rate of only approximately 40%, an additional 50% of the cuttings survived from the cutting stage to the rooted stage. Therefore, the new basil plant exhibits an ease of asexual reproduction not seen in prior plants.

The new basil plant also exhibits dramatically increased resistance to the devastating Fusarium wilt disease. When under attack by Fusarium wilt, a crop of the new basil plant has a die off of typically less than 10%. This is in sharp contrast to the 70% die-off expected of known sweet Italian basil varieties. Further, the new basil plant exhibits increased insect resistance, primarily to the root knot nematode. Due to its resistance to disease and insect, more of the rooted plants survive to maturity and are therefore available for harvest.

Figure 3:
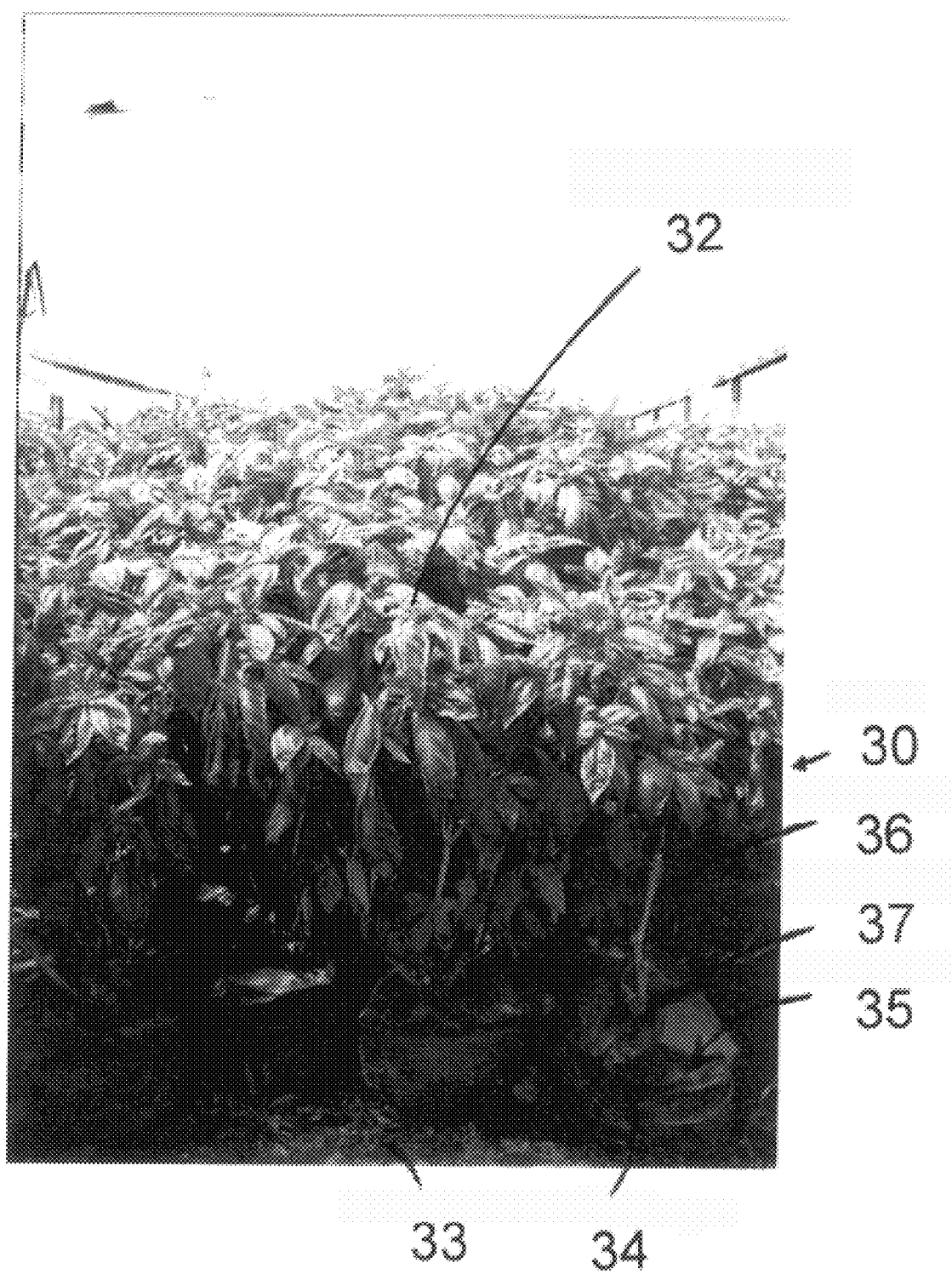
FIG. 3 of the accompanying photographic drawings illustrates a front view of a new basil plant showing the basil plants growing in above-ground containers.

The new basil plant has shown to produce a plant at an overall height of between two and a half to three feet, or more. Referring to FIG. 3, the basil plant 30 is shown being grown in above-ground containers 35. The rootball 34 of the basil plant 30 ends and the main stem 36 starts at the container top 37. As the container top 37 is approximately ten inches above ground level 33, the plant top 32, is positioned approximately 10 inches higher than if the basil plant 30 were planted in the ground.

Referring now to FIG. 1, basil plants 10 are shown adjacent a height scale 15. Basil plants 10, like basil plants 30, are planted in above ground containers. Therefore, the height scale 15 shows the height of the basil plant plus the height of the container. As can be seen in FIG. 1, the new basil plants 10 have a mature height approaching 4 feet, when measured including the container Allowing approximately 10 inches for the container, FIG. 1 shows that the basil plant 10 is nearly three feet tall. This is nearly a full foot taller than typical varieties of Sweet Italian basil. Further, the leaf-to-stem ratio is particularly high on the new basil plant; thereby providing more harvestable plant material per stem.

Indeed, the new plant exhibits harvestable productivity levels approximately twice the productivity of known Italian Sweet basil. For example, in summer the new basil plant produces approximately 19,300 pounds per acre per month, and in winter, can produce approximately 8,950 pounds per acre per month. Thereby the economic value of a stand of the new basil plants is at least twice as valuable as a stand of typical Sweet Italian basil.

This increase in productivity is due to several factors. First, as discussed above and shown in FIG. 1, the new basil plant is larger and has a better leaf to stem ratio than prior plants. Also, the increased resistance to disease and insects results in stronger more productive plants. Most significantly, the new basil plant grows much faster than prior plants. Indeed, rather than having eight to ten harvests as normally expected, the new basil plant is harvested anywhere from 15 to 25 times a season, with decreased harvesting intervals. Further, the new basil plant does not have to be grown as an annual, but may produce season to season. Therefore, the mature new basil plant has a dramatically longer period where it yields at a higher economic level.

Figure 2:
FIG. 2 of the accompanying photographic drawings illustrates a close-up view of the top of the new basil plant showing leaf ribbing and texture.

Also contributing to the increased productivity is the increased leaf size of the new basil plant. Referring now to FIGS. 1 and 2, a basil plant 10 and 20 is shown with main leaf 12 and 25. The main leaf 12 and 25, and the main leaf size generally, of the mature new basil plant is 3–4 inches in length. The color of the leaf is a light dark green to medium dark green, which is darker than the typical sweet Italian basil plant.

Further contributing to the increased productivity is the extended temperature range where the new basil plant produces at an acceptable economic level. For example, the new basil plant withstands temperatures down to 50° F. and still produces acceptable commercial yields. Even more dramatic is that the new basil plant provides exceptional production yields at temperatures exceeding 110° F.

Not only does the new basil plant produce well at these high temperatures, but it also has improved wilt resistance in high temperatures. Basil tops harvested in temperatures over 100° F. have exhibited substantially reduced wilting as compared to a typical basil plant. Indeed, no appreciable wilt is observed even at temperatures of 110° F.

Upon harvest, the basil tops taken from the new plants exhibit a shelf life of nearly one full week. This is in sharp contrast to the four day shelf life typical of prior basil. Such a dramatic increase in shelf life increases the commercial value of the new basil plant as less product is discarded due to wilting or blackening. Further, the product as purchased by the consumer appears fresher and therefore can demand a premium price.

Not only is the new basil plant producing at exceptional levels, but the quality of the harvested plant material is also exceptional. Basil, as a culinary herb, is used primarily for its appealing aroma and unique taste. The new basil plant has a very strong aroma. This very strong anise aroma can be initiated with only a slight brushing of the leaf surface. Indeed, it has even been observed that a light wind blowing across the leaf causes the new basil plant to emit pleasant aroma. Accompanying this unusually strong and easily produced aroma is an unusually strong basil flavor. The presence of such strong aroma and flavor indicate the presence of increased levels of essential and volatile oils over other known varieties.

NEW PLANT FEATURE OUTLINE

The following outline sets forth a number of features of the new plant. Color specification in parenthesis below were determined by reference to the RHS Colour Chart of the Royal Horticultural Society of London.

Type: A new variety of sweet Italian basil.

Breeding: Asexual reproduction from stock plants that were propagated from Sweet Italian basil seed.

Propagation: Holds its distinguishing characteristics through successive propagation by cuttings. Habit: Exceptional bushiness as shown in the drawings is due to the numerous branches, with nodes spaced every three to four inches along the main stem. Each node produces up to five individual leaves. The distance between nodes decreases from the base to the tip of the plant. The new basil plant is sustainable season to season.

Growth: Mature plant reaches an overall height of about two and a half to three feet. The new plant also exhibits dramatically increased growth rates allowing between 15 and 25 harvests per year.

Foliage: Leaves are unusually long with a mature length between three and four inches. There are opposite type leaves oval in shape with a slight cupping downward not only from the ribs but also interveinal. The texture of the leaf has a slight ripple. Young leaves show no serration on leaf edge but as leaves mature, a slight serration appears as shown in the drawing. The color of the leaf is a light dark green (132C) to a medium dark green.(135B)

Main Stems: Six to eight branches appear from the main stem. Nodes are spaced three to four inches apart on each stem with four to five shoots per node. The main stem is a light green.

Seed: Tiny dark brown seeds.

Harvesting Season: Year round depending on climate. The plant holds yield down to 50° F. and holds yield in excess of 110° F.

Flavor: Stronger anise flavor as compared to previous Sweet Italian basil.

Aroma: Strong anise aroma initiated by only a slight perturbation.

Essential Oils: Higher concentration of essential oils as compared to previous Sweet Italian basil.

Disease Resistance: Strong resistance to Fusarium wilt. Insect Resistance: Increased resistance to Root Knot Nematode. Productivity: Yield up to 19,300 pounds per acre per month in summer, and up to 8,950 pounds per acre per month in winter.

Use: Used as a culinary herb in either dried or fresh form.

Fresh Shelf Life: New basil plant exhibits a shelf life of nearly seven days at the store level.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed:

1. A variety of Sweet Italian basil plant grown from seed deposited as ATCC No. PTA-4151, said plant comprising:
   a main stem reaching a mature height of over 2.5 feet;
   nodes positioned on the main stem at a spacing of between approximately 3 inches to approximately 4 inches;
   leaves extending from the nodes, with at least one node having five leaves, wherein mature leaves have a length of approximately 3 inches to approximately 4 inches,
   wherein said basil plant does not have to be grown as an annual, and
   wherein said basil plant is harvestable between about 15 times and about 25 times each season.

2. The basil plant according to claim 1, wherein a plurality of said basil plants are planted into a basil field, the basil field producing at a rate of approximately 19,000 pounds per acre during summer months.

3. The basil plant according to claim 1, wherein a plurality of said basil plants are planted into a basil field, the basil field producing at a rate of approximately 8,900 pounds per acre during winter months.

4. The basil plant according to claim 1, wherein a plurality of said basil plants are planted into a basil field, the basil field having a die-off of less than approximately 10% when the basil field is attacked by Fusarium wilt.

5. The basil plant according to claim 1, wherein a plurality of transplantable plants prepared from cuttings of said basil plant are planted into a basil field, the basil field having a survivability rate of approximately 90% when basil cuttings are transplanted to the basil field.

6. A variety of Sweet Italian basil plant grown from seed deposited as ATCC No. PTA-4151, wherein said plant is resistant to Fusarium wilt at temperatures at or about 100° F. or hotter.

7. The basil plant according to claim 6, wherein the basil plant is harvestable between about 15 times and about 25 times each season.

8. The basil plant according to claim 1, wherein the basil plant is harvestable at temperatures over about 10 degrees F. and down to about 50 degrees F.

9. The basil plant according to claim 1, wherein during asexual reproduction the basil plant is rooted in less than about 7 days after cutting.

10. The basil plant according to claim 1, wherein the leaf has a color defined in a range from a light dark green (132C) to a medium dark green (135B).

11. The basil plant according to claim 1, wherein fresh cuttings from the basil plant exhibit a shelf life of approximately seven days at the store level.

12. The basil plant according to claim 1, wherein the basil plant is harvestable in successive years.

13. A variety of Ocimum basilicum grown from seed deposited as ATCC No. PTA-4151, wherein said variety does not have to be grown as an annual.

14. A variety of Sweet Italian basil plant grown from seed deposited as ATCC No. PTA-4151, wherein said plant is resistant to Fusarium wilt and to root knot nematode.

15. A variety of Sweet Italian basil plant grown from seed deposited as ATCC No. PTO-4151.

* * * * *